United States Patent [19]

Giannessi et al.

[11] Patent Number: 5,532,409

[45] Date of Patent: Jul. 2, 1996

[54] PROCESS FOR PRODUCING R-AMINOCARNITINE AND S-AMINOCARNITINE

[75] Inventors: Fabio Giannessi, Rome; Roberto Castagnani, Recanati; Francesco De Angelis, Rome; Maria O. Tinti, Rome; Domenico Misiti, Rome, all of Italy

[73] Assignee: Sigma-Tau Industrie Farmaceutiche Riunite S.p.A., Rome, Italy

[21] Appl. No.: 317,658

[22] Filed: Sep. 30, 1994

Related U.S. Application Data

[63] Continuation of Ser. No. 281,354, Jul. 27, 1994, abandoned.

[30] Foreign Application Priority Data

Jul. 29, 1993 [IT] Italy .................. RM93A0502

[51] Int. Cl.$^6$ .................................. C07C 229/00
[52] U.S. Cl. ............................................ 562/561
[58] Field of Search ................................. 562/561

[56] References Cited

U.S. PATENT DOCUMENTS 4,521,432  6/1985  Kananaru ...................... 562/561
5,041,643  8/1991  Tinti et al. .

*Primary Examiner*—Michael L. Shippen
*Attorney, Agent, or Firm*—Oblon, Spivak, McClelland, Maier & Neustadt

[57] ABSTRACT

A process for producing aminocarnitine is described, wherein methanesulfonylcarnitine is converted to a lactone which is reacted with an azide to give azidocarnitine. The catalytic hydrogenation of azidocarnitine gives aminocarnitine.

4 Claims, No Drawings

PROCESS FOR PRODUCING R-AMINOCARNITINE AND S-AMINOCARNITINE

CROSS REFERENCE TO RELATED APPLICATION

This is a continuation of application Ser. No. 08/281,354, filed Jul. 27, 1994, now abandoned.

The present invention relates to a process for producing R- and S-aminocarnitine.

Recently, the discovery of pharmacological properties of aminocarnitine (I, R=H) and certain acyl derivatives of aminocarnitine (I, R=acetyl, N-caproyl, palmitoyl) has aroused substantial interest.

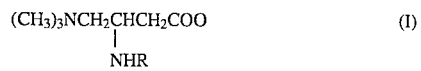

For example, D. L. Jenkins and O. W. Griffith have described antiketogenic and hypoglycemic effects of compounds (I) in their racemic form. Also, U.S. Pat. No. 4,521,432 (Takeda) describes the antiketogenic activity (with the accompanying possibility of applications in the treatment of diabetes) of an optically active derivative, (−)-N-acetyl aminocarnitine, inner salt ($[\alpha]_D^{25}=-17.4°$, c=1, $H_2O$). Analogous activity has been described for (+)-aminocarnitine chloride hydrochloride ($[\alpha]_D^{25}=+6.3°$, c=1, 1N AcOH).

Therefore, we feel that it is necessary to have available a process that provides both enantiomeric forms of aminocarnitine.

Actually, R(+)-aminocarnitine chloride can be obtained by acid hydrolysis of R(−)-N-acetyl aminocarnitine, isolated as a product during the cultivation of microorganisms of the genera Emericella or Aspergillus, or via a complex chemical procedure as described in the aforecited U.S. Pat. No. 4,521,432 (Takeda).

The synthesis of R(+)- and S(−)-aminocarnitine chloride starting from L- and from D-asparagine was described by Schinagawa in J. Med. Chem., 30: 1458 (1987). However, this synthetic method is rather complex. Indeed, it includes seven steps and involves the use of particularly dangerous reagents, such as diazomethane. Therefore, it is not a method suitable for industrial production, and was of value only insofar as it permitted assignment of the absolute configurations of (+)-aminocarnitine and (−)-aminocarnitine as R-aminocarnitine and S-aminocarnitine, respectively.

R-aminocarnitine chloride and S-aminocarnitine chloride can also be obtained by resolution of a racemic mixture of (±)-N-acetyl aminocarnitine, as described in SIGMA-TAU's Italian patent 1,205,758 corresponding to EP 287,523. However, in this case the starting material, (±)-N-acetyl aminocarnitine, was synthesized as described by D. Jenkins in J. Biol. Chem. 260: 14748 (1985), using a rather complex five-step procedure starting with a uracil derivative Alternatively, R(+)- and S(−)-aminocarnitine chloride can be obtained by resolution via silica gel chromatography or fractional crystallization of a diastereoisomer mixture consisting of N-[S(−) α-methylbenzyl]R(+) aminocarnitine benzylester chloride and N-[S(−) α-methylbenzyl]S(−)-aminocarnitine benzylester chloride or N-[R(+) α-methylbenzyl]R(+) aminocarnitine benzylester chloride and N-[R(+) α-methylbenzyl]S(−)-aminocarnitine benzylester chloride and subsequent de-benzylation of the isolated diastereoisomers as disclosed in SIGMA-TAU's Italian patent 1,231,751.

Also in this case the process is quite complex since it includes some silica gel chromatographies which may turn out particularly cumbersome if the process is carried out on an industrial scale.

All the drawbacks of the known procedures are overcome by the process for producing aminocarnitine inner salt according to the invention, which comprises the steps of:

(1) converting methanesulfonylcarnitine to a lactone by treating methanesulfonylcarnitine in a basic environment, e.g. by treating methanesulfonylcarnitine with an equimolar amount of $NaHCO_3$ in an aprotic polar solvent such as dimethylsulfoxide (DMSO), acetonitrile and dimethylformamide at 15°–50° C., for 3–12 hours;

(2) converting the lactone to azidocarnitine inner salt by treating the lactone for 2–6 hours, at 20°–30° C. with an equimolar amount of an azide selected from lithium azide, sodium azide, diphenylphosphorylazide and trimethylsilylazide;

(3) converting azidocarnitine to aminocarnitine inner salt via catalytic hydrogenation in the presence of 10% Pd/C, at 2–4 hydrogen atmospheres, for 8–18 hours.

It should be understood that, whereas in the following reaction scheme which shows the preparation of R(−)-aminocarnitine inner salt 4 from R(−)-methanesulfonylcarnitine 1, the process is described, for the sake of clarity, as a sequence of three distinct operating steps, the corresponding industrial process consists of a single step only.

When the process of the present invention is carried out as an industrial process, it is not necessary to isolate either the lactone 2 or the azide derivative 3

With reference to the following reaction scheme, $X^-$ can be any anion apt to impart solubility to the compound 1 in the reaction medium. For example $X^-$ is methanesulfonate.

REACTION SCHEME

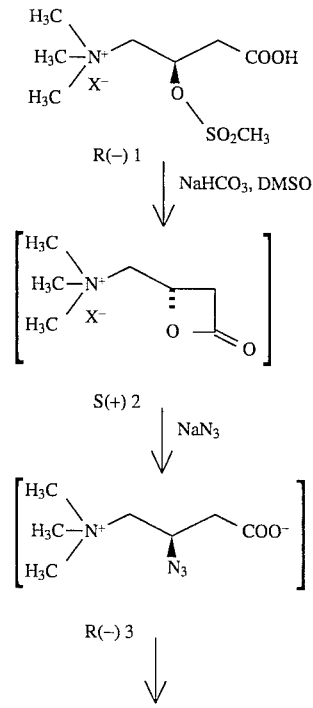

-continued
REACTION SCHEME

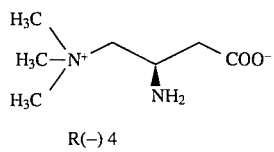

R(−) 4

EXAMPLE

Preparation of R(−)-aminocarnitine inner salt.

Sodium bicarbonate (0.5 g; 5.96 mmoles) was added to methanesulfonyl R(−)-carnitine methanesulfonate (2 g; 5.96 mmoles) in DMSO (100 mL). The resulting solution was kept under stirring at room temperature for 6 hours (till complete lactone formation, as monitored via HPLC and NMR). Sodium azide (0.387 g; 5.96 mmoles) was added to the reaction mixture and the resulting solution Was kept under stirring at room temperature for 2 hours.

Following precipitation and repeated treatments with $Et_2O$, a raw product containing R(−)-azidocarnitine inner salt was obtained.

R(−)-azidocarnitine inner salt $^1$H NMR ($D_2O$): δ4.48–4.38(m,1H,—$CHN_3$), 3.50–3.40(m,2H,—$CH_2N^{+Me}{}_3$), 3.2(s,9H,—$N^+Me_3$), 2.68–2.50(m,2H,—$CH_2COO^−$)

IR (Pure): ν(cm$^{-1}$) 2121 (—C—$N_3$), 1595 (—C=O)

HPLC

Column=nucleosil 5-SA; inner diameter=4 mm; length=200 mm

Eluant=$CH_3CN/KH_2PO_4$ 50 mM(65/35) pH 3.5 with $H_3PO_4$

Flow rate=0.75 mL/min

Retention time=13.02 min

Detector=RI Waters 410

The raw product thus obtained was subjected to catalytic hydrogenation in MeOH (20 mL) with 10% Pd/C (0.098 g) at three hydrogen atmospheres.

After one night, the reaction mixture was filtered on celite and the concentrated filtrate was percolated through IRC-50 resin (20 g) (which had been previously washed with 2% aqueous $NH_3$, reactivated with 2N HCl and eluted with $H_2O$ till neutrality), till complete elution of neutral and acidic impurities.

Following elution with a 2% aqueous $NH_3$ solution and eluate evaporation under vacuum. R(−)-aminocarnitine inner salt (0.53 g) was obtained. Yield=55%

The assignment of configuration was undertaken via HPLC using a CHIRALPAK-WM chiral column by comparison with a standard sample of known chirality.

Under the same analysis conditions the two enantiomers were well distinguishable.

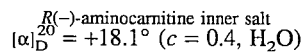

R(−)-aminocarnitine inner salt
$[\alpha]_D^{20} = +18.1°$ ($c = 0.4$, $H_2O$)

DSC=It decomposes in the temperature range from 140° to 210° C. Elementary analysis for $C_7H_{16}N_2O_2$ (K.F.= 6% $H_2O$)

|  | C | H | N |
|---|---|---|---|
| Calculated | 52.47 | 10.06 | 17.48 |
| Calculated with 6% $H_2O$ | 49.33 | 10.13 | 16.43 |
| Found | 49.15 | 10.42 | 16.32 |

$^1$H NMR ($D_2O$): δ 3.72–3.62(m, 1H,—$CHNH_2$),3.48–3.38(m, 2H,—$CH_2N^+Me_3$), 3.22(s, 9H,—$N^+Me_3$), 2.50–2.36(m, 2H.—$CH_2COO$)

HPLC

Column=CHIRALPACK-WM, Inner diameter=4.6 mm, length=250 mm temperature=50° C.

Eluant=$CuSO_4$ 1 mM+$NaClO_4$ 2 mM in $H_2O$, pH=3 with $HClO_4$

Flow rate=1 mL/min

Retention time=24.32 min

[R(−)-aminocarnitine inner salt, standard=24.17 min; S(+)-aminocarnitine inner salt standard=9.09 min]

Detector=UV Waters 996 λ=230 nm

Since the prior art references (EP 80695 and EP 127098, Takeda) relate to R(+)-aminocarnitine chloride hydrochloride, for the sake of analysis and comparison this salt was obtained by eluting the IRC-50 resin with a 1N HCl solution rather than a $NH_3$ solution.

The acidic excess was removed by shaking with slightly basic resins, such as LA2 (hexane solution), The aqueous phase was washed with hexane and finally evaporated under vacuum to give R(+)-aminocarnitine chloride hydrochloride (0.7 g).

Yield=50%.

The data relating to this compound were in agreement with those found in the relevant literature.

The enantiomeric excess, assessed with the method disclosed in Italian Pat. 1,231,751, was 100%.

We claim:

1. A process for producing aminocarnitine inner salt which comprises the steps of:

(1) converting methanesulfonylcarnitine to a lactone by treating methanesulfonylcarnitine in a basic environment;

(2) converting the lactone to azidocarnitine inner salt by treating the lactone with an azide for 2–6 hours, at 20°–30° C.; and (3) converting the azidocarnitine to aminocarnitine inner salt via catalytic hydrogenation in the presence of 10% Pd/C, at 2–4 hydrogen atmospheres, for 8–18 hours.

2. The process of claim 1 for producing R-aminocarnitine inner salt, wherein in step (1) methanesulfonylcarnitine is R-methanesulfonylcarnitine.

3. The process of claim 1 for producing S-aminocarnitine inner salt, wherein in step (1) methanesulfonylcarnitine is S-methanesulfonylcarnitine.

4. The process of claims 1, 2 or 3, wherein in step (2) the azide is selected from lithium azide, sodium azide, diphenylphosphorylazide and trimethylsilylazide.

* * * * *